United States Patent [19]

Zima et al.

[11] Patent Number: 5,393,901
[45] Date of Patent: Feb. 28, 1995

[54] AQUEOUS PROCESS FOR PREPARING AMIDO-CARBOXYLIC ACIDS

[75] Inventors: George C. Zima, Kingsport; T. Hugh Williams, Fall Branch; Gary P. Lutz, Kingsport, all of Tenn.; William C. Dickason, Batesville, Ark.

[73] Assignee: Eastman Chemical Company, Kingsport, Tenn.

[21] Appl. No.: 228,611

[22] Filed: Apr. 15, 1994

[51] Int. Cl.$^6$ .............................................. C07C 231/02
[52] U.S. Cl. ....................................... 554/69; 554/63; 554/68; 554/154; 554/161
[58] Field of Search ................... 384/68, 69, 154, 161, 384/63

[56] References Cited

U.S. PATENT DOCUMENTS

| | | | |
|---|---|---|---|
| 2,453,234 | 11/1948 | Keck | 260/534 |
| 2,844,611 | 7/1958 | Freudenberg | 584/63 |
| 2,956,068 | 10/1969 | Dohr et al. | 584/63 |

FOREIGN PATENT DOCUMENTS 648889  1/1951  United Kingdom .

Primary Examiner—José G. Dees
Assistant Examiner—Deborah D. Carr
Attorney, Agent, or Firm—John D Thallemer

[57] ABSTRACT

This invention relates to a process for preparing amido-carboxylic acids in water wherein hydrolysis and amidation reactions are conducted simultaneously in a single vessel. The process involves three steps. The first step involves heating at a temperature of 150° C.–300° C. for 2 to 10 hours, a mixture containing water, a nitrogen containing compound selected from the group consisting of a lactam and an amino acid, and a carboxylic acid or ester. The second step involves cooling the reaction mixture to obtain a two phase system containing an aqueous layer and an organic layer. The third step involves separating the amido-carboxylic acid containing organic layer from the aqueous layer. The presence of water aids in product isolation by phase separation and recycle of the reactants.

Amido-carboxylic acids are used to make bleach activators for detergents.

9 Claims, No Drawings

AQUEOUS PROCESS FOR PREPARING AMIDO-CARBOXYLIC ACIDS

FIELD OF INVENTION

This invention relates to a process for preparing amido-carboxylic acids in water wherein hydrolysis and amidation reactions are conducted simultaneously in one vessel. The process involves three steps. The first step involves heating at a temperature of 150° C.–300° C. for 2 to 10 hours, a mixture containing water, a nitrogen containing compound selected from the group consisting of a lactam and an amino acid, and a carboxylic acid or ester. The second step involves cooling the reaction mixture to obtain a two phase system containing an aqueous layer and an organic layer. The third step involves separating the amido-carboxylic acid containing organic layer from the aqueous layer. The presence of water aids in product isolation by phase separation and recycle of the reactants.

Amido-carboxylic acids are used to make bleach activators for detergents.

BACKGROUND OF THE INVENTION

Amido-carboxylic acids are industrial chemical intermediates for the preparation of many chemicals used in commerce. Amido-carboxylic acids are prepared by reacting a lactam with a carboxylic acid.

Amido-carboxylic acids are also prepared by reacting a carboxylic acid, carboxylic acid chloride, carboxylic acid anhydride or carboxylic acid ester with an amino carboxylic acid which is prepared by hydrolysis of a lactam. These processes to form amido-carboxylic acids are referred to as amidation reactions.

It is known to convert lactams by hydrolysis into the corresponding amino-carboxylic acids in the presence of hydrolysis promoting reagents such as hydrochloric acid. However, pure amino-acids are not directly obtained. In the case where hydrochloric acid is used as the promoting reagent, the amino-acid-hydrochloride is obtained and the separation of the free carboxylic acid is cumbersome and expensive.

U.S. Pat. No. 2,453,234 discloses a process for preparing an amino-carboxylic acid by hydrolyzing a lactam by means of at least 10 moles of water per mole of lactam to produce an amino-carboxylic acid. Great Britain Pat. No. 648,889 discloses a process for preparing amino-carboxylic acids by heating aliphatic or cycloaliphatic lactams in the presence of more than 20 moles of water per mole of lactam. U.S. Pat. No. 2,956,068 discloses a process for preparing amido-carboxylic acids by reacting a lactam with a free carboxylic acid in the presence of catalytic amounts of water. The reaction product is obtained as a solid crystal mass which is subsequently suspended in water and neutralized.

In contrast, the present inventors have unexpectedly discovered a process for preparing amido-carboxylic acids wherein lactam hydrolysis, carboxylic acid ester hydrolysis, and amidation reactions are conducted simultaneously. It is unexpected that an amido-carboxylic acid could form by amidation under hydrolysis conditions. The amido-carboxylic acids obtained by this process essentially contain one molecule of amino acid and one molecule of carboxylic acid.

SUMMARY OF THE INVENTION

Accordingly, it is one object of the present invention to provide a process for preparing amido-carboxylic acids.

Accordingly, it is another object of the invention to provide a process for preparing amido-carboxylic acids in water.

These and other objects are accomplished herein by a process for preparing amido-carboxylic acids wherein hydrolysis and amidation reactions are conducted simultaneously in water, said process comprising the steps of:

(A) reacting in one vessel at a temperature of 150° C.–300° C. for 2 to 10 hours, a mixture containing (1) a nitrogen containing compound selected from the group consisting of a lactam containing at least 3 carbon atoms per molecule, and an amino acid, provided the amino acid has the formula $NH_2(CRR')_nCOOH$ wherein n is 1–26, and R and R' are independently selected from the group consisting of hydrogen, unsubstituted or substituted $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl;

(2) 1 to 10 moles of a carboxylic acid compound per mole of the nitrogen containing compound, said carboxylic acid compound having 6 to 26 carbon atoms selected from the group consisting of a carboxylic acid, a carboxylic acid ester and combinations thereof; and (3) 10 to 50 moles of water per mole of the nitrogen containing compound, to form a reaction mixture containing an amido-carboxylic acid; and (B) cooling the reaction mixture formed in Step (A) to a temperature to achieve phase separation of an organic layer containing the amido-carboxylic acid, and an aqueous layer; and (C) separating the amido-carboxylic acid containing organic layer from the aqueous layer.

DESCRIPTION OF THE INVENTION

The process of the present invention involves three steps. In the first step, Step (A), water, a nitrogen containing compound selected from a lactam and an amino acid, and a carboxylic acid or ester thereof are combined in a reactor. The reactor must be able to be heated and must contain the pressure of the reaction. Preferably, the reactor is an autoclave. The reaction in Step (A), involves up to three of the following independent reactions which occur simultaneously: hydrolysis of the carboxylic acid ester forming a carboxylic acid and an alcohol, hydrolysis of the lactam forming an amino acid, and amidation of the carboxylic acid with the amino acid to form an amido-carboxylic acid. The alcohol formed by the hydrolysis of the carboxylic acid ester is removed by methods known in the art such as distillation.

Component (1) is a nitrogen containing compound selected from a lactam or an amino acid. Suitable lactam monomers contain at least 3 carbon atoms per molecule, preferably 4 to 7 carbon atoms per molecule. Suitable lactam monomers include butyrolactam, valerolactam, epsilon-caprolactam, beta-propiolactam, delta-valerolactam, and similar lactams. These lactams may be substituted at the nitrogen atom by lower hydrocarbon radicals containing for example, 1–3 carbon atoms. For example, methylcaprolactam may be used. Epsilon-caprolactam and substituted derivatives thereof are the preferred lactam monomers.

The amino acid has the general formula $NH_2(CRR')_nCOOH$ and is characterized by a basic amino group ($NH_2$) and an acidic carboxyl group (COOH). The letter n in the formula is 1-26, preferably 1-10. The R and R' groups are independently selected from hydrogen, unsubstituted or substituted straight chain or branched $C_1$-$C_{20}$ alkyl, unsubstituted or substituted $C_3$-$C_8$ cycloalkyl, $C_3$-$C_8$ alkenyl, $C_3$-$C_8$ alkynyl, and $C_6$-$C_{14}$ aryl.

The unsubstituted and substituted $C_3$-$C_8$ cycloalkyl groups mentioned above refer to cycloaliphatic hydrocarbon groups which contain 3 to 8 carbons in the ring, preferably 5 or 6 carbons, and these cycloalkyl groups substituted with one or two of $C_1$-$C_4$ alkyl, $C_1$-$C_4$ alkoxy, hydroxy or $C_1$-$C_4$ alkanoyloxy.

The $C_3$-$C_8$ alkenyl and $C_3$-$C_8$ alkynyl groups represent straight or branched chain hydrocarbon radicals containing 3 to 8 carbons in the chain and which contain a carbon-carbon double bond or a carbon-carbon triple bond, respectively.

The term "aryl" is used to include carbocyclic aryl groups containing up to fourteen carbons, e.g., phenyl and naphthyl, and those substituted with one or two groups selected from $C_1$-$C_4$-alkyl, $C_1$-$C_4$ alkoxy, $C_1$-$C_4$-alkoxycarbonyl, $C_1$-$C_4$-alkanoyloxy, $C_1$-$C_4$-alkanoylamino, halogen, cyano, $C_1$-$C_4$-alkylsulfonyl, $C_1$-$C_4$-alkylene-$(OH)_n$, O—$C_1$-$C_4$-alkylene-$(OH)_n$, —S—$C_1$-$C_4$-alkylene-$(OH)_n$, —$SO_2$—$C_1$-$C_4$-allkylene-$(OH)_n$, —$CO_2$—$C_1$-$C_4$-alkylene-$(OH)_n$, $SO_2N(R_{17})$-$C_1$-$C_4$-alkylene-$(OH)_n$, —$SO_2N(C_1$-$C_4$-alkylene-OH$)_2$, —$CON(R_{17})C_1$-$C_4$-alkylene-$(OH)_n$, —$CON(C_1$-$C_4$-alkylene-OH$)_2$, —$N(SO_2C_1$-$C_4$-alkyl)-alkylene-$(OH)_n$ or —$N(SO_2$ phenyl)-$C_1$-$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocyclic aryl hydrocarbon moiety containing up to fourteen carbons, e.g., o-, m- and p-phenylene, and those substituted with one or two groups selected from $C_1$-$C_4$-alkyl, $C_1$-$C_4$-alkoxy or halogen.

Component (2) is a carboxylic acid compound. The carboxylic acid compound is a carboxylic acid or carboxylic acid ester, or combination thereof, which contains an aliphatic, such as a straight branched chain or aliphatic radical, cycloaliphatic or hydroaromatic radical. The carboxylic acid or carboxylic acid ester has 6-26 carbon atoms, preferably 8-20 carbon atoms, and most preferably 8-10 carbon atoms. These radicals may be connected to the carboxyl group through an aromatic radical. The carboxylic acids and carboxylic acid esters may be straight or branched chain fatty acids of natural or synthetic origin which may be of a saturated or unsaturated nature. The carboxylic acids and esters can contain more than one carboxylic acid or ester group. Esters of carboxylic acids include, but are not limited to, the methyl, ethyl, propyl, and butyl ester of a carboxylic acid. The carboxylic acids and carboxylic acid esters may be used in pure form or else in the form of their mixtures as commercially available.

Examples of carboxylic acids and carboxylic acid esters are: caprylic acid, methyl caprylate, pelargonic acid, methyl pelargonate, capric acid, methyl caprate, isopropyl caprate, undecylic acid, lauric acid, palmitic acid, stearic acid, oleic acid, linoleic acid, behenic acid, terephthalic acid, dimethyl terephthalate, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Preferred carboxylic acids are capric and caprylic. Preferred carboxylic acid esters are methyl caprate and methyl caprylate.

Component (3) is water which includes tap water and distilled water. Distilled water is preferred since tap water may contain metal salts which in combination with the carboxylic acid could form surface active agents and inhibit isolation of the product.

The reaction of Step (A) may be carried out over a wide range of temperatures, but at temperatures below 150° C. the reaction rate of hydrolysis of the lactam monomer is very slow. On the other hand, it is generally not desirable to exceed temperatures above 300° C. inasmuch as polymerization of the lactam may take place. In addition, at such high temperatures, a higher operating pressure would be needed to contain the water. Accordingly, a temperature between 150°-300° C. is satisfactory. Temperatures of 200° to 250° C. are particularly desirable in the substantial absence of oxygen. The time of the reaction is generally 2 to 10 hours, preferably 4 to 8 hours. In the case where an ester of a carboxylic acid is used, alcohol generated by the hydrolysis of the ester is removed from the reactor by distillation.

The carboxylic acid compound is present in an amount of 1 to 10 moles, preferably, 1 to 5 moles per mole of the nitrogen containing compound. Most preferably, the carboxylic acid compound is present in an amount of 2 to 4 moles per mole of the nitrogen containing compound. Insufficient carboxylic acid compound results in the polymerization of the nitrogen containing compound. Although there is no critical higher limit to the amount of carboxylic acid compound, in practice one will not use a higher ratio than is strictly necessary to produce the desired results in any given case since to do so would render the process unnecessarily expensive from the point of view of recovering the desired product in pure form. The addition of water allows the ratio of the carboxylic acid compound to the nitrogen containing compound to be substantially lower by suppressing polymerization.

Water is present in an amount of 10 to 50 moles, preferably, 20 to 40 moles per mole of the nitrogen containing compound. Most preferably, the water is present in an amount of 30 to 35 moles per mole of the nitrogen containing compound. Insufficient water results in the polymerization of the nitrogen containing compound monomer. Although there is no critical higher limit to the amount of water, the use of greater than 50 mole percent water creates a situation where it is increasingly difficult to separate the small organic phase from the aqueous phase and would render the process unnecessarily expensive from the point of view of recovering the desired product in pure form. Most preferably, the molar ratio for the water, carboxylic acid, and nitrogen containing compound monomer is 33:3:1, respectively.

The second step, Step (B), involves cooling the reaction mixture to obtain a two phase system containing an aqueous layer and an organic layer. The temperature at which the aqueous layer and organic layer separate depends on the specific reactants, however, generally a temperature of less than 150° C. is required for phase separation. Preferably, the reaction mixture is cooled to a temperature of less than 100° C. and most preferably, 70°–90° C. Step (B) may be conducted in the same vessel as Step (A) in a batch process, or Step (B) may be conducted in a separate vessel using either a batch process or a continuous process. Cooling is accomplished by methods known in the art such as external cooling with water, ice or through the use a cooling jacket. The amino acids which are soluble in water become miscible with the organic phase at the reaction temperatures. In contrast, the carboxylic acids which are not soluble in water become at least partially miscible with the water phase at the reaction temperatures. Misibility of the phases allows the reaction to proceed more readily. Phase separation occurs upon cooling. The carboxylic acids remain in the organic phase and the amino acids and nitrogen containing compounds remain essentially in the water phase.

The third step, Step (C), involves separation of the organic phase which contains carboxylic acids and the amido-carboxylic acid product from the aqueous phase which contains amino acids, lactams, and water. Step (C) may be conducted in the same vessel as Step (A) and Step (B) in a batch process, or Step (C) may be conducted in a separate vessel using either a batch process or a continuous process. Separation is accomplished by methods known in the art such as decantation. The carboxylic acids and unreacted nitrogen containing compounds which remain in the organic phase are easily separated from the amido-carboxylic acid by distillation or crystallization and are recycled along with the aqueous phase.

Optionally, an acid catalyst in addition to the carboxylic acid, Component (3), may be added to the process to increase the speed of the reactions including the hydrolysis of the carboxylic acid ester forming a carboxylic acid and an alcohol, hydrolysis of the lactam forming an amino acid, and amidation of the carboxylic acid with the amino acid to form an amido-carboxylic acid. Suitable catalysts include carboxylic acids such as acetic acid or mineral acids such as sulfuric acid. Very small quantities of the catalyst are sufficient, such as from 0.001% to 1% based on the weight of the reactants in the reaction mixture.

The process of the present invention will be further illustrated by a consideration of the following examples, which are intended to be exemplary of the invention. All parts and percentages in the examples are on a weight basis unless otherwise stated.

EXAMPLES 1–6

Caprolactam, water and methyl decanoate were combined in a 300 ml rocking autoclave and heated for 4 hours. The amounts of the reactants were as follows:
A=Mole Ratio Caprolactam (1); Water (33.9); Methyl Decanoate (2.96); Decanoic Acid (0)
B=Mole Ratio Caprolactam (1); Water (33.9); Methyl Decanoate (2.96); Decanoic Acid (0.9)
C=Mole Ratio Caprolactam (1); Water (49.8); Methyl Decanoate (1.0); Decanoic Acid (0.1)
The reaction temperature is listed in Table I. When the reaction time was completed the autoclave was cooled and the product was removed from the autoclave. The aqueous layer was separated from the organic layer.

The products in the organic layer were isolated by liquid-liquid phase separation. Analytical data for the organic layer is summarized in Table II. Analytical data for the aqueous layer is summarized in Table II. Unreacted caprolactam and 6-aminocaproic acid, a reaction intermediate, were retained in the aqueous layer.

TABLE I

Summary of Hydrolysis of Caprolactam Using Methyl Decanoate and Different Levels of Decanoic Acid as Catalyst
Organic Layer Residues

| | Example | | | | | |
|---|---|---|---|---|---|---|
| | 1 | 2 | 3 | 4 | 5 | 6 |
| RX Temp. (°C.) | 200 | 200 | 250 | 250 | 250 | 275 |
| RX Time, (Hrs.) | 4 | 4 | 4 | 4 | 4 | 4 |
| Mole Ratio | A | B | A | B | C | C |
| Grams of Organic Layer | 82.26 | 83.98 | 83.17 | 83.77 | 55.57 | 56.72 |
| % Caprolactam | 8.2 | 7.1 | 6.6 | 6.2 | 11.4 | 12.7 |
| % Methyl Decanoate | 59.1 | 31.4 | 21.1 | 18.8 | 8.7 | 5.3 |
| % Decanoic Acid | 27.5 | 49.6 | 63.3 | 61.9 | 64.2 | 65.1 |
| % Amino Caproic Acid | 1.5 | 1.4 | <0.1 | 1 | <0.1 | 0.6 |
| % Acylcaprolactam | ND | ND | ND | ND | ND | ND |
| % Amido Caproic Acid | 2.9 | 7.8 | 7.3 | 10.4 | 13.24 | 12.2 |
| % Diamido Caproic Acid | ND | ND | ND | ND | ND | ND |

*ND refers to none detected

TABLE II

Summary of Hydrolysis of Caprolactam Using Methyl Decanoate and Different Levels of Decanoic Acid as Catalyst
Aqueous Layer Residues

| | Example | | | | | |
|---|---|---|---|---|---|---|
| | 1 | 2 | 3 | 4 | 5 | 6 |
| RX Temp., °C. | 200 | 200 | 250 | 250 | 250 | 275 |
| RX Time, Hours | 4 | 4 | 4 | 4 | 4 | 4 |
| Mole Ratio | A | B | A | B | C | C |
| Grams of Aqueous Layer | 95.38 | 83.45 | 83.87 | 83.8 | 130.32 | 156.76 |
| % Caprolactam | 6.5 | 2.5 | 2.3 | 1.6 | 3.5 | 4.1 |
| % Methyl Decanoate | 0.1 | 0.6 | 0.1 | 0.2 | 0.1 | 0.2 |
| % Decanoic Acid | 0.1 | 0.2 | 0.3 | 0.3 | 0.4 | 1.7 |
| % Amino | 2.3 | 1.1 | 1.1 | 0.7 | 1.0 | 1.2 |

TABLE II-continued

Summary of Hydrolysis of Caprolactam Using Methyl Decanoate and Different Levels of Decanoic Acid as Catalyst Aqueous Layer Residues

| | Example | | | | | |
|---|---|---|---|---|---|---|
| | 1 | 2 | 3 | 4 | 5 | 6 |
| Caproic Acid | | | | | | |
| % Acylcaprolactam | ND | <0.1 | ND | ND | ND | ND |
| % Amidocaproic acid | <0.1 | <0.1 | <0.1 | 0.1 | 0.1 | 0.4 |

*ND refers to none detected

COMPARISON EXAMPLES 7–12

Caprolactam, water and decanoic acid were combined in a 300 ml rocking autoclave and heated for 4 hours. The amounts of the reactants were as follows:

D = Mole Ratio Caprolactam (1); Water (33.8); Decanoic Acid (0.07)

E = Mole Ratio Caprolactam (1); Water (33.8); Decanoic Acid (0.99)

F = Mole Ratio Caprolactam (1); Water (33.9); Decanoic Acid (2.98)

The reaction temperature is listed in Table III. When the reaction time was completed the autoclave was cooled and the product was removed from the autoclave. The aqueous layer was separated from the organic layer.

The products in the organic layer were isolated by liquid-liquid phase separation. Analytical data for the organic layer is summarized in Table III.

TABLE III

Summary of Hydrolysis of Caprolactam Using Decanoic Acid as Catalyst and Reactant

| | Example | | | | | |
|---|---|---|---|---|---|---|
| | 7 | 8 | 9 | 10 | 11 | 12 |
| RX Temp., °C. | 200 | 200 | 250 | 250 | 250 | 250 |
| RX Time, Hours | 4 | 8 | 4 | 8 | 4 | 4 |
| Mole Ratio | D | D | D | D | E | F |
| % Caprolactam | 71.3 | 56.9 | 76.6 | 78.3 | 22.7 | 9.8 |
| % Decanoic Acid | 12.0 | 18.5 | 9.1 | 10.4 | 50.5 | 75.2 |
| % Amino Caproic Acid | 16.6 | 23.9 | 12.1 | 8.8 | 5.7 | 2.8 |
| % Acylcaprolactam | <0.1 | <0.1 | <0.1 | <0.1 | 0.4 | 0.6 |
| % Amido Caproic Acid | <0.1 | 0.7 | 2.1 | 2.0 | 14.8 | 10.6 |
| % Diamido Caproic Acid | ND | ND | ND | ND | 2.7 | <0.1 |

*ND refers to none detected

Table I and Table II set forth the preferred ratios of reactants in the process of the present invention. For example, at 33:1 water to nitrogen containing compound ratio approximately 80 grams of organic layer were recovered (Examples 1–4). At 49:1 water to nitrogen containing compound ratio approximately 50 grams of product were recovered (Examples 5–6).

The data in Table I clearly shows that the addition of decanoic acid as a catalyst increases the conversion of caprolactam to the C-10 amidoacid at lower temperatures (Examples 1 and 2). The addition of decanoic acid as a catalyst has less effect on the conversion of caprolactam to the C-10 amidoacid at higher temperatures (Examples 3 and 4).

The data in Tables I and III also indicate the amidocarboxylic acids essentially contain one molecule of amino acid and one molecule of carboxylic acid since the diamido acid is present in less than 0.1 percent. In addition, no measurable amount of higher oligomeric materials such as diamidoacid or triamidoacid or other impurities such as N-decanoylcaprolactam were formed. However significant quantities of these impurities were formed in Example 11 when the decanoic acid mole ratio was lowered to 1.

Many variations will suggest themselves to those skilled in this art in light of the above detailed description. All such obvious modifications are within the full intended scope of the appended claims.

What is claimed is:

1. A process for preparing amido-carboxylic acids wherein hydrolysis and amidation reactions are conducted simultaneously in water, said process comprising the steps of:

(A) reacting at a temperature of 150° C.–300° C. for 2 to 10 hours, a mixture containing (1) a nitrogen containing compound selected from the group consisting of a lactam containing at least 3 carbon atoms per molecule, and an amino acid, provided the amino acid has the formula $NH_2(CRR')_nCOOH$ wherein n is 1–26, and R and R' are independently selected from the group consisting of hydrogen, unsubstituted or substituted $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl;

(2) 1 to 10 moles of a carboxylic acid compound per mole of the nitrogen containing compound, said carboxylic acid compound having 6 to 26 carbon atoms selected from the group consisting of a carboxylic acid, a carboxylic acid ester and combinations thereof; and (3) 10 to 50 moles of water per mole of the nitrogen containing compound, to form a reaction mixture containing an amido-carboxylic acid; and (B) cooling the reaction mixture formed in Step (A) to a temperature to achieve phase separation of an organic layer containing the amido-carboxylic acid, and an aqueous layer; and (C) separating the amido-carboxylic acid containing organic layer from the aqueous layer.

2. A process for preparing amido-carboxylic acids wherein hydrolysis and amidation reactions are conducted simultaneously in water, said process comprising the steps of:

(A) reacting at a temperature of 150° C.–300° C. for 2 to 10 hours, a mixture containing (1) a nitrogen containing compound selected from the group consisting of a lactam containing 3 to 7 carbon atoms per molecule, and an amino acid, provided the amino acid has the formula $NH_2(CRR')_nCOOH$ wherein n is 1–10, and R and R' are independently selected from the group consisting of hydrogen, unsubstituted or substituted $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl;

(2) 1 to 5 moles of a carboxylic acid compound per mole of the nitrogen containing compound, said carboxylic acid compound having 8 to 20 carbon atoms selected from the group consisting of a carboxylic acid, a carboxylic acid ester and combinations thereof; and (3) 20 to 40 moles of water per mole of the nitrogen containing compound, to form a reaction mixture containing an amido-carboxylic acid; and (B) cooling the reaction mixture formed in Step (A) to a temperature of less than 150° C. to achieve phase separation of an organic layer containing the amido-carboxylic acid, and an aqueous layer; and (C) separating the amido-carboxylic acid containing organic layer from the aqueous layer.

3. A process for preparing amido-carboxylic acids wherein hydrolysis and amidation reactions are conducted simultaneously in water, said process comprising the steps of:

(A) reacting at a temperature of 200° C.–250° C. for 4 to 8 hours, a mixture containing
  (1) a lactam selected from the group consisting of butyrolactam, valerolactam, epsilon-caprolactam, beta-propiolactam, and delta-valerolactam; and
  (2) 2 to 4 moles of a carboxylic acid per mole of the lactam, said carboxylic acid being selected from the group consisting of caprylic acid, pelargonic acid, capric acid, undecylic acid, lauric acid, palmitic acid, stearic acid, oleic acid, behenic acid, terephthalic acid, phthalic acid, isophthalic acid, naphthalene-2,6-dicarboxylic acid, cyclohexanedicarboxylic acid, cyclohexanediacetic acid, succinic acid, adipic acid, and sebacic acid; and (3) 30 to 35 moles of water per mole of the lactam, to form a reaction mixture containing an amido-carboxylic acid; and (B) cooling the reaction mixture formed in Step (A) to a temperature of 70° C. to 90° C. to achieve phase separation of an organic layer containing the amido-carboxylic acid, and an aqueous layer; and (C) separating the amido-carboxylic acid containing organic layer from the aqueous layer by decantation.

4. The process of claim 2 wherein the carboxylic acid ester, component (2), is selected from the group consisting of methyl caprylate, methyl caprate, methyl pelargonate, isopropyl caprate, and dimethyl terephthalate.

5. The process of claim 4 wherein the carboxylic acid ester is selected from the group consisting of methyl caprylate and methyl caprate.

6. The process of claim 3 wherein the lactam, component (1), is epsilon-caprolactam.

7. The process of claim 3 wherein the carboxylic acid, component (2), is selected from the group consisting of capric acid and caprylic acid.

8. The process of claim 3 wherein the water, component (3), is distilled water.

9. The process of claim 3 wherein the molar ratio of water to carboxylic acid to lactam monomer is 33:3:1, respectively.

* * * * *